United States Patent
Akaishi

(10) Patent No.: US 9,655,820 B2
(45) Date of Patent: May 23, 2017

(54) HAIR DYE

(71) Applicant: MITSUBISHI PENCIL COMPANY, LIMITED, Shinagawa-ku, Tokyo (JP)

(72) Inventor: Tetsuaki Akaishi, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/965,274

(22) Filed: Dec. 10, 2015

(65) Prior Publication Data

US 2016/0166477 A1    Jun. 16, 2016

(30) Foreign Application Priority Data

Dec. 15, 2014    (JP) ................... 2014-252918

(51) Int. Cl.
| | | |
|---|---|---|
| *A61Q 5/10* | (2006.01) | |
| *A61K 8/04* | (2006.01) | |
| *A61K 8/72* | (2006.01) | |
| *A61Q 5/06* | (2006.01) | |
| *A61K 8/81* | (2006.01) | |
| *A61K 8/02* | (2006.01) | |
| *A61K 8/19* | (2006.01) | |

(52) U.S. Cl.
CPC ............ *A61K 8/044* (2013.01); *A61K 8/0241* (2013.01); *A61K 8/19* (2013.01); *A61K 8/72* (2013.01); *A61K 8/8158* (2013.01); *A61Q 5/065* (2013.01); *A61K 2800/412* (2013.01); *A61K 2800/4322* (2013.01); *A61K 2800/61* (2013.01)

(58) Field of Classification Search
CPC .... A61Q 5/065; A61K 8/8158; A61K 8/0241; A61K 8/19; A61K 8/72; A61K 2800/4322; A61K 2800/61; A61K 2800/412

See application file for complete search history.

(56) References Cited

U.S. PATENT DOCUMENTS

2003/0066142 A1    4/2003   Tsuchiya
2005/0226838 A1*  10/2005   Krause .................. A61K 8/736
                                                          424/70.13

FOREIGN PATENT DOCUMENTS

| JP | 60-004116 A | 1/1985 |
|---|---|---|
| JP | 2001-172141 A | 6/2001 |
| JP | 2007-320895 A | 12/2007 |

* cited by examiner

*Primary Examiner* — Eisa Elhilo

(74) *Attorney, Agent, or Firm* — Buchanan, Ingersoll & Rooney PC

(57) ABSTRACT

A hair dye comprising at least 0.3 to 2% by mass of at least one of acid dyes, 0.5 to 6% by mass of a film-forming resin, 15 to 55% by mass of alcohol having 7 or less carbon atoms and 20% by mass or more of water and having a pH modified to 2 to 5, wherein the hair dye contains particles having an average particle diameter of 0.3 to 3 μm is provided as a hair dye which does not require washing of the hairs immediately after used and which is excellent not only in a hair dyeing property immediately after applied but also such a cumulative hair dyeing property as gradually dyeing the hairs at every frequency of repeating use thereof.

4 Claims, No Drawings

HAIR DYE

This Nonprovisional application claims priority under 35 U.S.C. §119(a) on Patent Application No. 2014-252918 filed in Japan on 15 Dec. 2014, the entire contents of which are hereby incorporated by reference.

BACKGROUND OF THE INVENTION

1. Field of the Invention

The present invention relates to a cumulatively dyeing hair dye which does not require washing of the hairs immediately after used and which not only is excellent in a hair dyeing property immediately after applied but also gradually dye the hairs at every frequency of repeating use thereof.

2. Description of the Conventional Art

Permanent hair dyes such as hair colors and oxidizing hair dyes, and semi-permanent hair dyes such as hair manicure and acid hair dyes which have so far usually been used have such large defects that not only hair dyes are complicated and consume time in dyeing operation in use but also the circumference, the cloths and the skin of persons applied are dyed.

Accordingly, such a large load that hair dyes have to be applied usually in beauty solons or hair dyes have to be applied by users themselves in bathing is exerted on the users.

Known as a hair dye which can reduce the loads described above and which can cumulatively dye hairs by easily repeating use are, to refer to, for example, patent document 1, 1) a cumulatively dyeing temporary hair dye which comprises 0.01 to 3% by weight of an acid dye as a colorant, 0.1 to 10% by weight of a nonionic or anionic silicone resin, 3 to 20% by weight of a hair dyeing auxiliary, 30 to 80% by weight of "low class alcohol" which means generally alcohol having 7 or less carbon atoms in Japan, and 5 to 50% by weight of water and which has a pH of 2 to 5 and a viscosity of 100 mPa·s or less, and a production process for the same; to refer to patent document 2, 2) a hair-dyeing composition which comprises 40 to 95% by weight of volatile "low class alcohol", 2 to 10% by weight of a thickener, 2 to 30% by weight of a hair dyeing auxiliary, carbon black, and at least one dye of a triphenylmethane dye, an azo dye, a quinoline dye, a xanthene dye, an indigoid dye and an anthraquinone dye and which is modified in a pH value to 1.5 to 4.5; and to refer to patent document 3, 3) a hair dye which comprises 0.4 to 3% by weight of at least one of water-soluble dyes, 0.5 to 7% by weight of a nonionic or anionic silicone resin, 0.4 to 4% by weight of carbon black, 0.5 to 6% by weight of an acrylic copolymer resin, 15 to 55% by weight of "low class alcohol" and 20% by weight or more of water and which is modified in a pH to 2 to 5.

The hair dye of patent document 1 is a hair dye having an excellent cumulative dyeing property, but the colorant is only the acid dye, and the problem that the acid dye is a little inferior in a temporary coloring performance for white hairs and that the dyed parts look a little lighter than hairs in the periphery depending on the light source are partially involved therein.

Further, in the hair dye and the like disclosed in patent document 2, the water resistance after applied is hard to be obtained, and when the water resistance is tried to be enhanced, involved therein are such many problems that dispersion stability of the carbon black is reduced and that aggregates are formed with the acid dye.

Also, the hair dye of patent document 3 is a hair dye having an excellent cumulative dyeing property, but the partial problem that a hue of the carbon black is slightly changed under a small pH environment to bring about a slight deviation between hues in temporarily dyeing and cumulatively dyeing has been involved therein.

Patent document 1: Japanese Patent Application Laid-Open No. 2001-172141 (claims, examples and others)
Patent document 2: Japanese Patent Application Laid-Open No. Sho. 60-4116 (claims, examples and others)
Patent document 3: Japanese Patent Application Laid-Open No. 2007-320895 (claims, examples and others)

SUMMARY OF THE INVENTION

In light of the problems of the conventional art described above, the present invention intends to solve the problems, and an object thereof is to provide a hair dye in which particles such as a pigment can stably be dispersed even under a small pH environment, which does not require washing the hairs immediately after used, which is excellent not only in a hair dyeing property immediately after applied but also such a cumulative hair dyeing property as gradually dyeing the hairs at every frequency of repeating use thereof, which does not bring about a deviation between hues in temporarily dyeing and cumulatively dyeing, and which is excellent in a water resistance and usability.

Means for Solving the Problems

Intensive investigations repeated by the present inventors on the problems of the conventional art described above have resulted in finding that a hair dye which meets the object described above is provided by a hair dye comprising at least an acid dye, a film-forming resin, alcohol having 7 or less carbon atoms and water and having a pH modified to a specific range, wherein the hair dye contains particles having an average particle diameter modified to a specific range, and thus the present invention has been come to complete.

That is, the present invention comprises the following items (1) to (4).

(1) A hair dye comprising at least: 0.3 to 2% by mass of at least one of acid dyes; 0.5 to 6% by mass of a film-forming resin; 15 to 55% by mass of alcohol having 7 or less carbon atoms; and 20% by mass or more of water; and having a pH modified to 2 to 5, wherein the hair dye contains particles having an average particle diameter of 0.3 to 3 μm.
(2) The hair dye as described in the above item (1), wherein the particles having an average particle diameter of 0.3 to 3 μm comprise at least one selected from the group consisting of black iron oxide, red iron oxide, yellow iron oxide, carbon black, sumi, silica and titanium oxide.
(3) The hair dye as described in the above item (1) or (2), wherein the particles having an average particle diameter of 0.3 to 3 μm is subjected to surface treatment of 2 to 15% by mass with silica.
(4) The hair dye as described in any one of the above items (1) to (3), comprising a thickener as a settling inhibitor for the particles.

Effect of the Invention

According to the present invention, provided is a hair dye in which particles such as a pigment can stably be dispersed even under a small pH environment, which does not require washing the hairs immediately after used, which is excellent in not only a hair dyeing property immediately after applied but also a cumulative hair dyeing property in gradually dyeing the hairs at every frequency of repeating use thereof, which does not bring about a deviation between hues in temporarily dyeing and cumulatively dyeing, and which is excellent in a water resistance and usability.

DETAILED DESCRIPTION OF THE PREFERRED EMBODIMENTS

The embodiment of the present invention shall be explained below in detail.

The hair dye of the present invention comprises at least 0.3 to 2% by mass of at least one of acid dyes, 0.5 to 6% by mass of a film-forming resin, 15 to 55% by mass of alcohol having 7 or more carbon atoms and 20% by mass or more of water and having a pH modified to 2 to 5, wherein the hair dye contains particles having an average particle diameter of 0.3 to 3 μm.

At least one of acid dyes among legal colorants used usually for cosmetics can be used for the acid dye used in the present invention.

The specific examples of the acid dye include at least one of Red No. 2, Red No. 3, Red No. 102, Red No. 104, Red No. 105, Red No. 106, Yellow No. 4, Yellow No. 5, Green No. 3, Blue No. 1, Blue No. 2, Red No. 201, Red No. 206, Red No. 227, Red No. 230, Red No. 231, Red No. 232, Orange No. 205, Orange No. 207, Yellow No. 202, Yellow No. 203, Green No. 201, Green No. 204, Green No. 205, Blue No. 202, Blue No. 203, Blue No. 205, Brown No. 201, Red No. 401, Red No. 502, Red No. 503, Red No. 504, Red No. 506, Orange No. 403, Yellow No. 402, Yellow (1) of No. 403, Yellow No. 406, Yellow No. 407, Green No. 401, Green No. 402, Purple No. 401, and Black No. 401, each alone or a mixture of two or more kinds thereof, hereinafter the same shall apply.

A content of the acid dye is 0.3 to 2% by mass, hereinafter referred to merely as "%", preferably 0.4 to 1.5% based on a total amount of the hair dye.

If a content of the acid dye is less than 0.3%, the hair dyeing effect is not sufficiently obtained. On the other hand, if the content exceeds 2%, the system becomes unstable due to the influence of solubility thereof in a mixed solvent of water and the alcohol having 7 or more carbon atoms, and stain on such as the skin is liable to be caused. Accordingly, both are not preferred.

The film-forming resin used in the present invention shall not specifically be restricted as long as the film formed has a water resistance and includes, for example, polymers comprising a nonionic monomer unit and/or an anionic monomer unit.

The nonionic monomer includes, for example, such as aromatic hydrocarbons of a styrene derivative, and alkyl methacrylate ester, but the nonionic monomer shall not be restricted to the above examples. The anionic monomer includes, for example, such as methacrylic acid, acrylic acid, and maleic acid, but the anionic monomer shall not be restricted to the above examples.

Also, the film-forming resin may be a block copolymer with, for example, a polysiloxane unit such as polydimethylsiloxane in order to enhance the water resistance and the touch. The film-forming resin is blended in order to improve the secondary adhesive property and the water resistance.

Preferably, the film-forming resin includes such as copolymers of polydimethylsiloxane with methacrylic acid and/or esters of methacrylic acid and aliphatic alcohols having 6 or less carbon atoms, and alcohol-soluble silicone resins.

A content of the above film-forming resins is 0.5 to 6%, preferably 1 to 3% based on a total amount of the hair dye.

If a content of the film-forming resin is less than 0.5%, the water resistance is unsatisfactory, and the less content is not preferred. On the other hand, if a content of the film-forming resin exceeds 6%, the resin cannot be dissolved in the mixed solvent of water and the alcohol having 7 or more carbon atoms, or the touch after applied on the hairs is deteriorated, and therefore the excessive content is not preferred.

At least one of volatile alcohol having 7 or less carbon atoms such as, for example, ethanol, 1-propanol, butanol, 2-propanol, and isobutanol can be used as the alcohol having 7 or less carbon atoms used in the present invention, and ethanol is preferred from the viewpoints of a safety, a drying property, an odor and the like.

A content of the above alcohols having 7 or less carbon atoms is 15 to 55%, preferably 30 to 50% based on a total amount of the hair dye.

If a content of the alcohols having 7 or less carbon atoms is less than 15%, the hair dye is reduced in a drying property, and therefore the less content is not preferred. On the other hand, if the content exceeds 55%, the hair dye is reduced in a cumulative hair dyeing effect, and therefore the excessive content is not preferred.

The balance of the hair dye in the present invention is adjusted by water such as refined water, distilled water, deionized water, purified water and tap water.

A content of water has to be 20% or more and is preferably 30 to 50% based on a total amount of the hair dye.

If a content of water is less than 20%, the hair dye is reduced in solubility and reduced as well in a hair dyeing effect, and therefore it is not preferred. On the other hand, if it exceeds 50%, the water-resistant film-forming resin contained is a little reduced in stability and slightly decreased in a drying property.

The particles having an average particle diameter of 0.3 to 3 μm used in the present invention are used in order to improve the temporary dyeing property of white hairs immediately after applied. The "average particle diameter" in the present invention including examples described later is a value obtained by measuring a 10 weight % dispersion of the particles by means of a particle diameter analyzer FPAR-1000, manufactured by Otsuka Electronics Co., Ltd., and a particle diameter distribution measuring equipment Microtrac SIA, manufactured by MicrotracBEL Corp.

No problem shall be involved in the particles used in the present invention as long as the particles are inorganic particles of iron oxides such as black iron oxide, yellow iron oxide, and red iron oxide, carbon black, titanium oxide and zinc oxide, and pigment particles of sumi, silica, ultramarine, mica and talc, and the inorganic pigment particles of iron oxides such as black iron oxide, yellow iron oxide, and red iron oxide, and carbon black are suited in terms of a masking power and a cost.

In the hair dye of the present invention, a pH of the hair dye is designed, as described later, to as small as 2 to 5 in order to improve a hair dyeing property by the acid dye. The foregoing particles having an average particle diameter of 0.3 to 3 μm used do not damage the effects of the present invention due to the influence thereof, however, the problem that the deterioration advances a little with the aging to allow the color tone to slightly change has been partially involved therein. Further intense investigations on the above problem have resulted in finding that it is desirable to use the particles having an average particle diameter of 0.3 to 3 μm which are subjected preferably on a surface to silica treatment so that the particles can readily be dispersed even in the mixed solvent of water and the alcohol having 7 or less carbon atoms and are further prevented from being affected by the pH.

In the present invention, the particles subjected to the silica treatment described above can be produced by subjecting inorganic particles of iron oxides such as black iron oxide, yellow iron oxide, and red iron oxide, carbon black and titanium oxide, and particles of sumi to surface treatment by such as a spray drying method, and a vapor deposition method, and if possible, commercially available products can be used.

A concentration of the silica used for the surface treatment of the particles is desirably 2 to 15%, preferably 2 to 12% in terms of a mass conversion before and after the treatment.

If a treating concentration of the silica is less than 2%, the treating amount is insufficient to bring about a change in the quality of the particles and caking thereof in a certain case due to the aging. On the other hand, if the treating concentration exceeds 15%, an effect of a hue provided to the particles themselves is reduced, and the temporary hair dyeing property is slightly decreased in a certain case.

An average particle diameter of the particles described above in the present invention or the particles subjected to the silica treatment is generally 0.3 to 3 μm, preferably 0.5 to 2 μm.

If an average particle diameter of the particles is less than 0.3 μm, the particles are hard to be produced from the viewpoints of the production technique and the cost, and particularly the silica-treated particles are technically hard to be produced and are not suited to the uses in terms of the cost. On the other hand, if the average particle diameter exceeds 3 μm, the particles adhered to the hairs are readily peeled off in combing the hairs by a comb, and therefore the larger diameter is not preferred.

A content of the particles having an average particle diameter of 0.3 to 3 μm described above in the present invention is 0.5 to 5%, preferably 1 to 3% based on a total amount of the hair dye.

If a content of the above particles is less than 0.5%, the temporary hair dyeing property is unsatisfactory. On the other hand, if the content exceeds 5%, a treating concentration of the silica, the use feeling and the touch are deteriorated, and therefore the excessive content is not preferred.

A thickener can be contained as a settling inhibitor for the particles used in the present invention. the thickener includes, for example, hydroxyethyl cellulose, xanthane gum, gellan gum, guar gum, hydroxypropyl guar gum, sclerotium gum, carbomer, and an (acryloyldimethyltaurin ammonium/beheneth-25 methacrylate) cross-polymer, and among the thickeners, the (acryloyldimethyltaurin ammonium/beheneth-25 methacrylate) cross-polymer is suited from the viewpoints of a lipid solubility in a small pH range and a stable thickening property.

A content of the thickener in the present invention is 1.5 to 3%, preferably 1.8 to 2.5% based on a total amount of the hair dye.

If a content of the above thickener is less than 1.5%, the settling inhibition effect of the particles is unsatisfactory, and the less content is not preferred. On the other hand, if the content exceeds 3%, the hair dye is solidified in the form of a gel in a certain case, and the excessive content is not preferred in terms of usability.

A hair dyeing auxiliary is preferably contained in the hair dye of the present invention from the viewpoint of further exerting a hair dyeing effect.

The hair dyeing auxiliary which can be used includes, for example, at least one of such as benzyl alcohol, phenylethyl alcohol, phenoxyethanol, propylene carbonate, propylene glycol, ethoxydiglycol, N-methylpyrrolidone, and N-methyl-2-pyrrolidone.

A content of the above hair dyeing auxiliary is 2 to 20%, suitably 5 to 15% based on a total amount of the hair dye.

If a content of the above hair dyeing auxiliary is less than 2%, the effect of further exerting a hair dyeing is unsatisfactory. On the other hand, if the content exceeds 20%, the drying property after applying the hair dye is reduced, and a risk of color transfer onto cloths and the like is increased, so that the excessive content is not preferred.

The hair dye of the present invention has to be modified to a pH of 2 to 5 in order to improve a dyeing property and prevent skin irritation and skin dyeing trouble, and the hair dye is preferably modified to a pH of 2.5 to 4.0.

If a pH of the hair dye is less than 2, the skin dyeing property is increased, and therefore the less pH is not preferred. On the other hand, if the pH exceeds 5, the hair dyeing property is reduced, and the larger pH is not preferred.

In the present invention, the pH can be modified by using organic acids such as formic acid, acetic acid, lactic acid, tartaric acid, malic acid, citric acid, and glycolic acid, inorganic acids or salts thereof, and in a certain case, bases such as triethanolamine.

The hair dye of the present invention can suitably contain, in addition to at least one of the acid dyes, the film-forming resin, the alcohol having 7 or less carbon atoms, water and the particles having an average particle diameter of 0.3 to 3 μm each described above, the other materials, for example, such as various surfactants, an antiseptic agent, a UV absorber, an antioxidant, a reduction inhibitor, a chelating agent, an oil component, a perfume, animal and vegetable extracts, as long as the effects of the present invention are not damaged.

The hair dye of the present invention can be prepared by an ordinary method and can be produced by blending the respective components such as at least one of the acid dyes, the film-forming resin, the alcohol having 7 or less carbon atoms, water and the particles having an average particle diameter of 0.3 to 3 μm each described above in the ranges of the contents described above, and homogeneously stirring and mixing them.

For example, an alcohol phase of the film-forming resin and the alcohol having 7 or less carbon atoms, and an aqueous phase of the acid dye and water are stirred respectively to homogeneous solutions by means of a general purpose disperser, and then the alcohol phase and the aqueous phase are mixed. Then, a pH modifier and a thickener are further added thereto and stirred to a homogeneous solution by means of such as a disperser, followed by adding the particles having an average particle diameter of 0.3 to 3 μm and stirring the mixture by means of such as a homomixer, whereby the hair dye can be prepared.

When the hair dye of the present invention constituted in the manner described above is used, a general purpose applicator for hairs can be used, and the applicator for hairs shall not specifically be restricted in a shape and a structure and includes, for example, applicators such as an applicator equipped with a valve device of a knock type, an applicator of a mascara type, an applicator of a tube type, and an applicator equipped with a piston pressing mechanism.

The hair dye of the present invention constituted in the manner described above contains at least 0.3 to 2% by mass of at least one of the acid dyes, 0.5 to 6% by mass of the film-forming resin, 15 to 55% by mass of the alcohol having 7 or less carbon atoms and 20% by mass or more of water and has a pH modified to 2 to 5, wherein the hair dye contains the particles having an average particle diameter of 0.3 to 3 μm, whereby obtained is the hair dye in which particles of such as a pigment can stably be dispersed even under a small pH environment, which does not require washing the hairs immediately after used, which is excellent in not only a hair dyeing property immediately after applied but also a cumulative hair dyeing property in gradually dyeing the hairs at every frequency of repeating use thereof, which does not bring about a deviation between hues in temporarily dyeing and cumulatively dyeing, and which is excellent in a water resistance and usability.

EXAMPLES

Next, the present invention shall be explained in further details with reference to examples, but the present invention shall not be restricted by the following examples.

Examples 1 to 15 and Comparative Examples 1 to 9

An alcohol phase and an aqueous phase were stirred respectively to homogeneous solutions by means of a general purpose disperser in blend formulations in which the total amount was set to 100% as shown in the following Tables 1 and 2, and then the alcohol phase and the aqueous phase were mixed. Further, a pH modifier and a thickener were added thereto and stirred to a homogeneous solution by means of a disperser, and then pigment particle were added and stirred by means of a homomixer to prepare the respective hair dyes.

The respective hair dyes obtained in Examples 1 to 15 and Comparative Examples 1 to 9 by the method described above were used to evaluate a pH, a hair dyeing property immediately after applied, a cumulative hair dyeing property, a drying property, a water resistance, a touch and a temporal stability of the hair dyes respectively by the following methods.

The results thereof are shown in the following Tables 1 and 2.

Measuring Method of a pH of the Hair Dye:

The respective hair dyes obtained in Examples 1 to 15 and Comparative Examples 1 to 9 by the method described above were used to measure a pH at 25° C. by means of a glass electrode pH meter.

Evaluating Method of Hair Dyeing Property Immediately after Applied:

The respective hair dyes obtained 0.2 g were applied on a hair bundle 1 g mixed with white hairs of 20% and dried, and then the hair bundle was used to evaluate whether or not the white hairs were masked according to the following evaluation criteria.

Evaluation Criteria:

A: hair bundles were masked at such a level that a difference between the white hairs and the black hairs was not recognized.
B: hairs were unevenly dyed but were almost masked with dyeing color.
C: hairs were dyed with dyeing color, but the white hairs could be confirmed to be present.
D: hairs were scarcely dyed.

Evaluating Method of Cumulative Hair Dyeing Property:

An operation in which the respective hair dyes obtained 0.2 g were applied on a hair bundle 1 g of white hairs of 100% and dried and in which the hair bundle was then washed twice was repeated five times, and then the hair dyeing state of the hair bundle was evaluated according to the following evaluation criteria.

Evaluation Criteria:

A: comparable to commercially available oxidation hair dye, that is, hair color.
B: comparison with commercially available oxidation hair dye shows that the hair dyeing property was a little inferior.
C: comparison with commercially available oxidation hair dye shows that the hair dyeing property was clearly inferior.
D: hairs were scarcely dyed.

Evaluating Method of Drying Property:

The respective hair dyes obtained 0.1 g were applied on a hair bundle 1 g of white hairs of 100% and left standing at normal temperature for 10 minutes, and then a filter paper was pressed on the hair bundle to evaluate a state in which the color was transferred onto the filter paper according to the following evaluation criteria.

Evaluation Criteria:

A: the hair dye was not at all transferred onto the filter paper.
B: the hair dye was slightly transferred onto the filter paper.
C: the hair dye was a little intensely transferred onto the filter paper.
D: the hair dye was intensely transferred onto the filter paper.

Evaluating Method of Water Resistance:

The respective hair dyes obtained 0.1 g were applied on a hair bundle 1 g of white hairs of 100% and left standing at normal temperature for 120 minutes, and then a filter paper wetted with water was pressed on the hair bundle to evaluate a state in which the color was transferred onto the filter paper according to the following evaluation criteria.

Evaluation Criteria:

A: the hair dye was not at all transferred onto the filter paper.
B: the hair dye was slightly transferred onto the filter paper.
C: the hair dye was a little intensely transferred onto the filter paper.
D: the hair dye was intensely transferred onto the filter paper.

Evaluating Method of Touch:

The respective hair dyes obtained 0.1 g were applied on a hair bundle 1 g of white hairs of 100% and left standing at normal temperature for 120 minutes, and then a stickiness, a stiffness and a combing property of the hair bundle were sensory evaluated according to the following evaluation criteria.

Evaluation Criteria:

A: good, no stickiness and stiffness was felt and no flaking in combing was caused.
B: flaking in combing was slightly caused, but no stickiness and stiffness were was felt.
C: flaking in combing was frequently caused a little, and stickiness and stiffness was felt.
D: flaking in combing was frequently caused, and uncomfortable stickiness and stiffness was felt.

Evaluating Method of Temporal Stability:

The respective hair dyes obtained were weighed into a sample bottle of 30 ml and left standing for 1 month under the environment of 50° C., and then the presence or absence of the precipitates of the pigment, the aggregates and the like on the bottom of the bottle was visually evaluated according to the following evaluation criteria.

Evaluation Criteria:

A: the color of the liquid was homogeneous, and no precipitate was confirmed at the bottom.
B: the color of the liquid was homogeneous, and a trace of the precipitates was confirmed at the bottom but homogeneously dispersed by re-stirring.
C: a supernatant was observed on an upper part of the liquid, and the precipitates were confirmed at the bottom but homogeneously dispersed by re-stirring.
D: a supernatant was observed on an upper part of the liquid, and the precipitates were confirmed at the bottom and were not homogeneously dispersed even by re-stirring.

TABLE 1

| Hair dye composition: | | Example | | | | | | | |
|---|---|---|---|---|---|---|---|---|---|
| | materials | 1 | 2 | 3 | 4 | 5 | 6 | 7 | 8 |
| Alcohol phase | Ethanol | 42.50 | 50.00 | 20.00 | 42.50 | 42.50 | 42.50 | 42.50 | 42.50 |
| | Benzyl alcohol | 10.00 | 5.00 | 5.00 | 10.00 | 10.00 | 10.00 | 10.00 | 10.00 |
| | Propylene carbonate | | 5.00 | 5.00 | | | | | |
| | Film-forming resin *1 | 2.50 | 2.50 | 2.50 | 1.00 | 3.00 | 2.50 | 2.50 | 2.50 |
| Aqueous phase | Black No. 401 | 0.20 | 0.20 | 0.20 | 0.20 | 0.20 | 0.20 | 0.20 | 0.20 |
| | Purple No. 401 | 0.30 | 0.30 | 0.30 | 0.30 | 0.30 | 0.30 | 0.30 | 0.30 |
| | Orange No. 205 | 0.40 | 0.40 | 0.40 | 0.40 | 0.40 | 0.40 | 0.40 | 0.40 |
| | Refined water | 37.80 | 30.30 | 60.30 | 39.30 | 37.80 | 38.80 | 36.80 | 38.30 |
| pH modifier | Glycolic acid | | | | 2.30 | 2.30 | | | 2.30 |
| | Lactic acid | 2.30 | 2.30 | 2.30 | | | 2.30 | 2.30 | |
| | Triethanolamine | | | | | | | | |
| Particles | 2% silica-treated black iron oxide *2 | | | 1.00 | | 1.00 | | | |
| | 12% silica-treated black iron oxide *3 | 1.00 | 1.00 | | 1.00 | | 0.50 | 1.50 | 1.00 |
| | 2% silica-treated red iron oxide *4 | | | 1.00 | | 1.00 | | | |
| | 12% silica-treated red iron oxide *5 | 1.00 | 1.00 | | 1.00 | | 0.50 | 1.50 | 1.00 |
| | 2% silica-treated carbon black *6 | | | | | | | | |
| | 10% silica-treated titanium oxide *7 | | | | | | | | |
| | Silica bead *8 | | | | | | | | |
| | Black iron oxide (non-treated) | | | | | | | | |
| | Red iron oxide (non-treated) | | | | | | | | |
| Thickener | (Acryloyldimethyl-taurin ammonium/beheneth-25 methacrylate) cross-polymer *9 | 2.00 | 2.00 | 2.00 | 2.00 | 2.00 | 2.00 | 2.00 | 1.50 |
| <Total: % by mass> | | 100.00 | 100.00 | 100.00 | 100.00 | 100.00 | 100.00 | 100.00 | 100.00 |
| pH of hair dye | | 2.97 | 3.04 | 3.15 | 2.74 | 2.69 | 3.11 | 3.08 | 3.04 |
| Evaluation | Hair dyeing property immediately after applied | A | B | A | A | B | B | A | B |
| | Cumulative hair dyeing property | A | B | A | A | B | A | A | B |
| | Drying property | B | A | C | B | B | B | B | B |
| | Water resistance | A | B | B | B | A | A | B | B |
| | Touch | B | B | B | B | C | A | C | B |
| | Temporal stability (50° C.-1M) | A | A | B | A | A | A | A | B |

| Hair dye composition: | | Example | | | | | | |
|---|---|---|---|---|---|---|---|---|
| | materials | 9 | 10 | 11 | 12 | 13 | 14 | 15 |
| Alcohol phase | Ethanol | 42.50 | 42.50 | 42.50 | 42.50 | 42.50 | 42.50 | 42.50 |
| | Benzyl alcohol | 10.00 | 5.00 | 20.00 | 10.00 | 10.00 | 10.00 | 10.00 |
| | Propylene carbonate | | | | | | | |
| | Film-forming resin *1 | 2.50 | 2.50 | 2.50 | 2.50 | 2.50 | 2.50 | 2.50 |
| Aqueous phase | Black No. 401 | 0.20 | 0.20 | 0.20 | 0.20 | 0.20 | 0.20 | 0.20 |
| | Purple No. 401 | 0.30 | 0.30 | 0.30 | 0.30 | 0.30 | 0.30 | 0.30 |
| | Orange No. 205 | 0.40 | 0.40 | 0.40 | 0.40 | 0.40 | 0.40 | 0.40 |
| | Refined water | 36.80 | 42.80 | 27.80 | 39.60 | 34.60 | 34.60 | 37.80 |
| pH modifier | Glycolic acid | 2.30 | | | 0.50 | 5.00 | 5.00 | |
| | Lactic acid | | 2.30 | 2.30 | | | | 2.30 |
| | Triethanolamine | | | | | | | |
| Particles | 2% silica-treated black iron oxide *2 | | 1.00 | 1.00 | | | | |
| | 12% silica-treated black iron oxide *3 | 1.00 | | | 1.00 | 1.00 | | |
| | 2% silica-treated red iron oxide *4 | | 1.00 | 1.00 | | | | |
| | 12% silica-treated red iron oxide *5 | 1.00 | | | 1.20 | 1.00 | 1.00 | |
| | 2% silica-treated carbon black *6 | | | | 0.80 | | | |
| | 10% silica-treated titanium oxide *7 | | | | | | 0.50 | |
| | Silica bead *8 | | | | 0.50 | | | |
| | Black iron oxide (non-treated) | | | | | | | 1.00 |

TABLE 1-continued

|  |  |  |  |  |  |  |  |  |
|---|---|---|---|---|---|---|---|---|
|  | Red iron oxide (non-treated) |  |  |  |  |  |  | 1.00 |
| Thickener | (Acryloyldimethyl-taurin ammonium/beheneth-25 methacrylate) cross-polymer *9 | 3.00 | 2.00 | 2.00 | 2.00 | 2.00 | 2.00 | 2.00 |
|  | <Total: % by mass> | 100.00 | 100.00 | 100.00 | 100.00 | 100.00 | 100.00 | 100.00 |
|  | pH of hair dye | 3.22 | 3.04 | 3.11 | 3.55 | 2.38 | 2.38 | 2.99 |
| Evaluation | Hair dyeing property immediately after applied | B | B | B | A | B | B | B |
|  | Cumulative hair dyeing property | B | B | A | B | A | A | C |
|  | Drying property | B | A | B | B | B | B | B |
|  | Water resistance | B | B | B | B | B | B | B |
|  | Touch | C | B | B | B | B | B | C |
|  | Temporal stability (50° C.-1M) | A | A | B | A | B | B | C |

TABLE 2

| Hair dye composition: | | Comparative Example | | | | | | | | |
|---|---|---|---|---|---|---|---|---|---|---|
|  | materials | 1 | 2 | 3 | 4 | 5 | 6 | 7 | 8 | 9 |
| Alcohol phase | Ethanol | 60.00 | 9.00 | 42.70 | 40.50 | 42.50 | 42.50 | 42.50 | 42.50 | 12.50 |
|  | Benzyl alcohol | 5.00 | 5.00 | 10.00 | 10.00 | 10.00 | 10.00 | 10.00 | 10.00 | 2.00 |
|  | Propylene carbonate | 5.00 | 5.00 |  |  |  |  |  |  |  |
|  | Film-forming resin *1 | 2.50 | 2.50 | 0.30 | 7.00 | 2.50 | 2.50 | 2.50 | 2.50 | 2.50 |
| Aqueous phase | Black No. 401 | 0.20 | 0.20 | 0.20 | 0.20 | 0.05 | 0.60 | 0.20 | 0.20 | 0.20 |
|  | Purple No. 401 | 0.30 | 0.30 | 0.30 | 0.30 | 0.08 | 0.90 | 0.30 | 0.30 | 0.30 |
|  | Orange No. 205 | 0.40 | 0.40 | 0.40 | 0.40 | 0.10 | 1.20 | 0.40 | 0.40 | 0.40 |
|  | Refined water | 20.30 | 71.30 | 39.80 | 35.30 | 38.47 | 36.00 | 36.10 | 30.10 | 75.80 |
| pH modifier | Glycolic acid |  |  | 2.30 | 2.30 |  |  |  | 10 |  |
|  | Lactic acid | 2.30 | 2.30 |  |  | 2.30 | 2.30 |  |  | 2.30 |
|  | Triethanolamine |  |  |  |  |  |  | 4.00 |  |  |
| Particles | 2% silica-treated black iron oxide *2 |  | 1.00 |  |  | 1.00 | 1.00 |  |  | 1.00 |
|  | 12% silica-treated black iron oxide *3 | 1.00 |  | 1.00 | 1.00 |  |  | 1.00 | 1.00 |  |
|  | 2% silica-treated red iron oxide *4 |  | 1.00 |  |  | 1.00 | 1.00 |  |  | 1.00 |
|  | 12% silica-treated red iron oxide *5 | 1.00 |  | 1.00 | 1.00 |  |  | 1.00 | 1.00 |  |
| Thickener | (Acryloyldimethyl-taurin ammonium/beheneth-25 methacrylate) cross-polymer *9 | 2.00 | 2.00 | 2.00 | 2.00 | 2.00 | 2.00 | 2.00 | 2.00 | 2.00 |
|  | <Total: % by mass> | 100.00 | 100.00 | 100.00 | 100.00 | 100.00 | 100.00 | 100.00 | 100.00 | 100.00 |
|  | pH fof hair dye | 2.95 | 2.83 | 3.01 | 3.05 | 2.94 | 3.04 | 5.25 | 1.97 | 2.87 |
| Evaluation | Hair dyeing property immediately after applied | C | B | B | B | C | A | C | C | B |
|  | Cumulative hair dyeing property | C | B | B | C | C | B | D | B | D |
|  | Drying property | A | D | C | C | B | C | C | C | D |
|  | Water resistance | B | C | D | A | B | D | C | C | B |
|  | Touch | C | D | D | D | D | D | C | D | C |
|  | Temporal stability (50° C.-1M) | D | D | C | D | C | D | D | D | C |

*1 to *9 in Table 1 and Table 2 described above show the followings.
*1: alkyl acrylate/dimethicone copolymer
*2: average particle diameter: 2 μm, SIH-2 BLACK No. 710P, manufactured by DAITO KASEI KOGYO CO., LTD.
*3: average particle diameter: 2 μm, SYMPHOLIGHT BW, manufactured by JGC Catalysts and Chemicals Ltd.
*4: average particle diameter: 0.6 μm, SIH-2 RED No. 211P, manufactured by DAITO KASEI KOGYO CO., LTD.
*5: average particle diameter: 0.5 μm, SYMPHOLIGHT RW, manufactured by JGC Catalysts and Chemicals Ltd.
*6: average particle diameter: 0.3 μm, 2% silica-treated carbon black, trial product, produced by a spray drying method
*7: average particle diameter: 0.4 μm, SYMPHOLIGHT WW, manufactured by JGC Catalysts and Chemicals Ltd.
*8: average particle diameter: 2 μm, SILICA MICRO READ P-500, manufactured by JGC Catalysts and Chemicals Ltd.
*9: (acryloyldimethyltaurin ammonium/beheneth-25 methacrylate) cross-polymer, Aristoflex HMB, manufactured by Clariant (Japan) K.K.

As apparent from the results shown in Table 1 and Table 2 described above, it has become clear that the hair dyes prepared in Examples 1 to 15 falling in the scope of the present invention are excellent in a hair dyeing property immediately after applied, a cumulative hair dyeing property, a drying property, a water resistance, a touch and a temporal stability as compared with the hair dyes prepared in Comparative Examples 1 to 9 out of scope of the present invention and that the hair dyes in which the above advantages are consistent to a high degree are obtained.

Further, it has been found from the evaluation results of the hair dyeing property immediately after applied and the cumulative hair dyeing property that the respective hair dyes prepared in Examples 1 to 15 do not bring about a deviation between hues in temporarily dyeing and cumulatively dyeing even under a small pH environment and are excellent in a temporary hair dyeing performance and a cumulative hair dyeing performance of white hairs.

In contrast, to observe individually the comparative examples, Comparative Examples 1, 2 and 9 are cases in which a content of the alcohol having 7 or less carbon atoms is out of scope of the present invention; Comparative Examples 3 and 4 are cases in which a content of the film-forming resin is out of scope of the present invention; Comparative Examples 5 and 6 are cases in which a content of the acid dye is out of scope of the present invention; and Comparative Examples 7 and 8 are cases in which a content of a pH of the hair dye is out of scope of the present invention. It has been found that in the above cases, effects of the present invention cannot be exerted.

The invention claimed is:

1. A hair dye comprising at least: 0.3 to 2% by mass of at least one of acid dyes; 0.5 to 6% by mass of a film-forming resin; 15 to 55% by mass of alcohol having 7 or less carbon atoms; and 20% by mass or more of water; and having a pH modified to 2 to 5,
   wherein the hair dye contains particles having an average particle diameter of 0.3 to 3 μm and being subjected to surface treatment of 2 to 15% by mass with silica.

2. The hair dye as described in claim 1, wherein the particles having an average particle diameter of 0.3 to 3 μm comprise at least one selected from the group consisting of black iron oxide, red iron oxide, yellow iron oxide, carbon black, sumi, silica and titanium oxide.

3. The hair dye as described in claim 1, comprising a thickener as a settling inhibitor for the particles.

4. The hair dye as described in claim 2, comprising a thickener as a settling inhibitor for the particles.

* * * * *